United States Patent
Lemme

(10) Patent No.: US 12,154,568 B2
(45) Date of Patent: *Nov. 26, 2024

(54) CONVERSATIONAL ARTIFICIAL INTELLIGENCE DRIVEN METHODS AND SYSTEM FOR DELIVERING PERSONALIZED THERAPY AND TRAINING SESSIONS

(71) Applicant: John Lemme, Spring Branch, TX (US)

(72) Inventor: John Lemme, Spring Branch, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/171,334

(22) Filed: Feb. 18, 2023

(65) Prior Publication Data

US 2023/0197225 A1    Jun. 22, 2023

Related U.S. Application Data

(63) Continuation of application No. 16/773,083, filed on Jan. 27, 2020, now Pat. No. 11,587,562.

(51) Int. Cl.
| | |
|---|---|
| *G10L 15/22* | (2006.01) |
| *G06V 10/70* | (2022.01) |
| *G06V 40/10* | (2022.01) |
| *G06V 40/20* | (2022.01) |
| *G09B 7/02* | (2006.01) |
| *G09B 19/00* | (2006.01) |
| *G10L 13/00* | (2006.01) |
| *G10L 15/24* | (2013.01) |
| *G16H 15/00* | (2018.01) |

(52) U.S. Cl.
CPC ............. *G10L 15/22* (2013.01); *G06V 10/70* (2022.01); *G06V 40/10* (2022.01); *G06V 40/25* (2022.01); *G09B 7/02* (2013.01); *G09B 19/003* (2013.01); *G10L 13/00* (2013.01); *G10L 15/24* (2013.01); *G16H 15/00* (2018.01); *G10L 2015/223* (2013.01); *G10L 2015/225* (2013.01)

(58) Field of Classification Search
CPC ........ G09B 19/003; G09B 7/02; G06V 40/10; G06V 40/25; G10L 13/00; G10L 15/22; G10L 15/24; G10L 2015/223; G10L 2015/225

See application file for complete search history.

(56) References Cited

U.S. PATENT DOCUMENTS

| | | | |
|---|---|---|---|
| 8,715,176 B2 * | 5/2014 | Lemme .................. | G16H 40/63 345/581 |
| 10,448,866 B1 * | 10/2019 | German .................. | G10L 15/22 |

(Continued)

*Primary Examiner* — Douglas Godbold
(74) *Attorney, Agent, or Firm* — Hinckley Allen & Snyder; Stephen Holmes

(57) ABSTRACT

A user directed verbal interactive method and system for requesting a evaluation and obtaining a customized verbal therapy routine based on the evaluation obtained. The method and system allow users to interact with an artificial intelligence agent by answering a series of system directed questions that guides the users through evaluation and treatment of physical pain using a customized verbal interaction and delivery regimen. Users verbally engage with the artificial intelligence agent to create respective profiles. The system develops therapies based on their current physiological state and profile. The users are then delivered verbal therapy prompts through the system to implement the developed therapy routines.

12 Claims, 7 Drawing Sheets

(56) References Cited

U.S. PATENT DOCUMENTS

| | | | |
|---|---|---|---|
| 2007/0179816 A1* | 8/2007 | Lemme | G16H 20/30 482/8 |
| 2012/0130651 A1* | 5/2012 | Papadimitriou | G01N 27/9046 702/35 |
| 2012/0330109 A1* | 12/2012 | Tran | A61B 5/389 600/509 |
| 2016/0183687 A1* | 6/2016 | Hoyt | A61B 5/6891 297/217.2 |
| 2018/0137250 A1* | 5/2018 | Ding | G16H 20/00 |
| 2018/0358021 A1* | 12/2018 | Mistica | G16Z 99/00 |
| 2019/0214134 A1* | 7/2019 | Bates | G06N 20/00 |
| 2019/0259500 A1* | 8/2019 | Abou | G16H 10/20 |
| 2020/0114207 A1* | 4/2020 | Weldemariam | H04L 51/02 |
| 2020/0129838 A1* | 4/2020 | Chen | A61B 5/0205 |
| 2020/0152330 A1* | 5/2020 | Anushiravani | A61B 5/11 |
| 2020/0164250 A1* | 5/2020 | Lutz | G10L 15/26 |
| 2020/0227161 A1* | 7/2020 | Hanson | G06N 3/08 |
| 2021/0233652 A1* | 7/2021 | Owen | G16H 80/00 |
| 2021/0272585 A1* | 9/2021 | Han | G16H 15/00 |
| 2021/0316111 A1* | 10/2021 | Hattori | A61B 5/0507 |
| 2021/0394369 A1* | 12/2021 | Oh | B25J 11/0005 |

* cited by examiner

CONVERSATIONAL ARTIFICIAL INTELLIGENCE DRIVEN METHODS AND SYSTEM FOR DELIVERING PERSONALIZED THERAPY AND TRAINING SESSIONS

CROSS-REFERENCE TO RELATED APPLICATIONS

This application is a continuation of U.S. patent application Ser. No. 16/773,083, filed Jan. 27, 2020.

BACKGROUND OF THE DISCLOSURE

The present invention relates generally to an automated system for the delivery of personalized therapy and training sessions without any physical examination. More specifically, the present invention relates to an automated system whereby a user interacts with and is monitored by a conversational artificial intelligence (AI) agent (in form of voice only and/or avatar) and further whereby monitored responses and behaviors are analyzed by the AI system to develop, deliver and implement ongoing personalized activity, physical therapy, and/or behavior recommendations for the user.

Due to sedentary societies, and postural positions that are detrimental to the human body, there is a need for proper movement to offset negative stimulus. With proper sequenced body positions and muscular contraction of deep postural muscles, the body can readily heal itself. Without such proper movement, compensations, limitations, pain and ailments are inevitable. Unfortunately, most medical and non-medical treatments for pain and other ailments only treat the symptom, and not the underlying cause. Therefore, symptom relief is only temporary, while misalignments and dysfunctions remain.

Personal self-help systems are a fast-growing technological area. There is a critical need in society for individuals to be able to take control and initiative to proactively seek assistance with physical ailments and to improve both their physical and emotional well-being.

SUMMARY OF THE INVENTION

The implementation of physical therapy routines, exercise routines, weight loss, strength training and behavior modification for remedying the various symptoms suffered by an individual is known in the prior art. Treatment typically requires an extensive in-person physical examination for proper diagnosis and thereafter in-person application of proven therapeutic exercises and modality sciences. The exercises are usually prescribed and delivered to an individual in person by licensed therapists, physical therapists and/or athletic trainers.

Once the therapy routine or work routine is prescribed, the physical therapist must make sure the individual understands how to correctly accomplish the physical exercises in the routine. To do this, the physical therapist or exercise instructor will typically demonstrate the exercises to the individual and provide written and verbal instructions for subsequent reference. An important aspect of improvement results from properly repeating the exercises at given intervals with proper technique. However, unless patient actively visit a provider's office on a routine appointment schedule, patient compliance is often lax or non-existent.

There is therefore a need for a system that allows a user to interactively input personal information regarding their condition, to obtain customized therapy routines and to have those routines delivered to the user on a consistent basis. Moreover, there is a further need to deliver those routines in a more personal and instructive manner similar to visiting a therapist in person.

In this regard, the present invention provides for an interactive verbally directed method and system for inputting personal data, requesting a evaluation, generating customized therapy routines and interactively delivering those routines to the user by natural human language interactive prompts and instructions, all without the need for an in-person physical examination. The method and system of the present invention is an innovative technique through which a user is enabled to interact verbally with an artificial intelligence agent to facilitate the evaluation and treatment of physical pain using a customized verbal interactive system. This form of therapeutic self-exercise restores optimum anatomical, physiological and neurological function to the human body.

Unlike practices such as physical therapy, massage therapy, chiropractic and other pain-treatment therapies, the system and method of the present invention does not use hands-on manipulations or physical agents. The interaction is entirely artificial, language-based verbal interaction. Nevertheless, the invention herein effectively helps change posture, symptoms, and lives, by putting control of one's health back into the hands of the individual rather than creating dependence on a human practitioner or system. Furthermore, the present system utilizes therapeutic techniques that are identified via an artificial intelligence agent to assist in better directing the proper selection of a treatment regimen. This is a key factor that allows the present pain elimination and condition prevention programs to be fully interactive in an electronic platform. It further allows the method and system of the present invention to replicate the process of personal in-clinic programs by providing personalized verbal interactive sessions via an artificial intelligence agent delivered through any voice activated automated personal assistant system. These individualized therapy sessions or routines are created on demand and followed up on a regular schedule to meet each individual's specific needs. Moreover, a key aspect for widespread use and implementation is the ability of a single treatment system to quickly, reliably and simultaneously analyze data from multiple patients or users, develop diagnoses, create therapy sessions or routines and monitor progress. Such a system provides a unique improvement with simultaneous processing of multiple patient/user data. In-person or real-time video-based treatments require one-to-one interaction and analysis and the undivided attention of a licensed professional to assess a condition and deliver treatment. Scalability for one professional, assessing and treating multiple patients at the same time is not practical on a human functional level. One or two patients at a time may be possible, but tens or hundreds or thousands at the same time is not practically possible for a single human or even several humans. The present system allows tens, hundreds or thousands of users/patients to be assessed and treated at the same time.

The method and system of the present invention is implemented entirely through a verbal interactive user interface (can use video also—for gait and posture analysis) that delivers to the user a series of verbally directed exercises specifically tailored to their needs based on an artificial intelligence agent that also performs an interactive analysis to evaluate the user described symptoms. The artificial intelligence agent then determines, based on the user input answers, the probable muscle dysfunctions and imbalances that are causing the user's symptom(s). The system then develops a recommended routine, converts the routine to a verbal set of interactive instructions, and delivers the verbal instructions to the user through the voice activated personal assistant device.

As noted above, the key features of the present system is an interactive verbal user interface whereby a user accesses the system using voice activation and voice interaction. More specifically, once assistance is requested, the user builds a personal profile through a verbal interaction with an artificial intelligence agent that requests personal data such as age, weight, and sex, identification of the problem or symptom by selecting body areas, rating the severity of the pain or problem, identifying posture type using the personalized postural image upload interface where system posture ID is used (the posture of the user is determined by the system via its camera or uploaded images), identifying muscular imbalances and biomechanics deviations where the system gait ID is used (the gait of the user is captured by the system using its camera), identifying lifestyle issues, as well as listing how long the symptom has existed, when the symptoms first appeared, what body positions and activities make it worse, the symptom's effect on work and personal life including days missed from work, listing modalities, practitioners, and assessments for symptoms, listing medications both over-the-counter and prescription being taken for symptoms, listing evaluation, diagnostic tests, and surgeries for symptoms, listing prognosis for symptom and whether or not surgery has been recommended, and understanding of overall physical condition and why the pain symptoms exist. As the user progresses by answering the questions and providing the required information, the artificial intelligence agent applies logic rules via algorithms and complex patterns, to further identify relevant areas of inquiry to tailor and selects a coordinated series of predefined therapy routines designed to systematically correct posture and muscular imbalances and relieve symptoms. The system implements hundreds of deterministic rules, applied simultaneously and instantaneously though algorithms to analyze and provide diagnoses. The equivalent level of training and the application of such regimen and rules is simply not something that is capable by most professionals. Furthermore, the determination of probable muscular imbalances and diagnosis is not practical without a physical examination and/or advanced training in specific therapies which are not known by all care providers.

Accordingly, it is an object of the present invention to provide an interactive voice-controlled, artificial intelligence-based system and method for simultaneously developing user profiles, performing user evaluations, and generating tailored work, exercise, physical therapy, and/or behavioral modification routines for a plurality of individuals or users. It is another object of the present invention to provide an artificial intelligence agent that interactively creates a customized work, exercise, physical therapy and/or behavioral modification routine that can be delivered to an individual through currently available voice activated personal assistant systems as are widely implemented today. Yet another object of the present invention is to provide an artificial intelligence based agent via voice activated personal assistant systems to create a customized work, exercise or physical therapy routine, athletic training program, yoga or other exercise-based regimen that is able to verbally interact and follow up with the users on a regular basis. It is another object of the present invention to provide a method for creating a customized work, exercise or physical therapy routine that requires very little interaction with ordinary computer systems and which is easy to operate, comparatively as effective and significantly more cost effective compared to in-person therapy evaluation and treatment.

These together with other objects of the invention, along with various features of novelty that characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention.

DETAILED DESCRIPTION OF THE EXEMPLARY EMBODIMENTS

Figure 1:
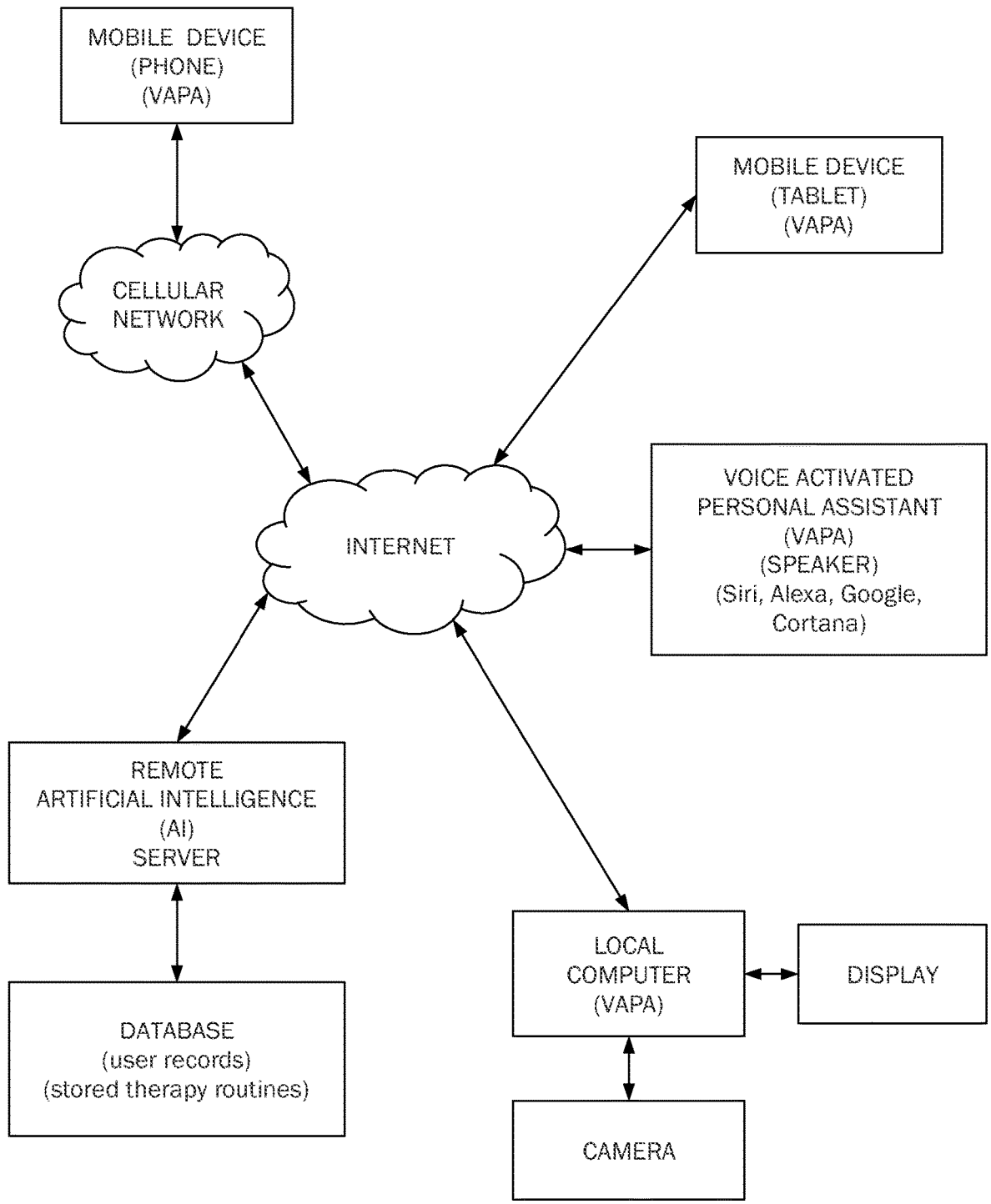
FIG. 1 is a schematic block diagram of an overall electronic communication system in accordance with the teachings of the present invention.

As was stated above, the present invention provides for a voice-directed interactive method and system 100 for developing a user profile, interactively building the user profile, generating an evaluation of the profile, and creating a customized therapy, exercise, behavior modification routine, etc. based on the user profile. While, for purposes of ease of description, the specification my refer to implementation of the system and method for a single user, it should be understood and noted that the intention of the invention is that the system is effective for, and should be implemented for simultaneous use by tens, hundreds and thousands of users. In this manner, the system provides a highly valuable and unique treatment modality whereby a single treatment system can simultaneously treat multiple users at the same time with the same effectiveness as a personal one-to-one treatment. This type of scalability, for hundreds of users, is not possible on a practical basis with a single or even several professional practitioners.

The method and system of the present invention is an innovative technique through which a user(s) is/are enabled to verbally interact with an artificial intelligence agent to facilitate data capture, and the evaluation and treatment of physical pain, as well as other physical and emotional issues using a customized verbally delivered regimen. The user(s)

primarily engage(s) with the artificial intelligence agent via voice activated personal assistant (VAPA) systems, such as Siri™, Alexa™, Google™, Cortana™, and/or another computer interface to provide additional still image and video input (Siri™, Alexa™, Google™, and Cortana™ are registered trademarks of their respective parent corporations).

The goal of the present invention is to verbally construct user profiles and then verbally deliver a customized therapy routine directly to each user in manner that allows each user to easily implement and complete the therapy while also providing each user with meaningful feedback and progress tracking. The method of providing a user with a customized therapy routine generally includes the initial establishment of a user account which is stored in a remote database 102. With the user account established, a user activates a conversational, artificial-intelligence (AI) agent software application running on a remote server 104, that verbally prompts a user to provide personal information regarding their physical attributes and directs the user 12 to respond to a variety of inquiries to obtain information regarding the user's physical condition, activity level, anatomical posture, pain symptoms, etc. As the user responds, the AI agent software 104 converts the user responses to usable data points, stores the data points in the database 102 and further tailors the inquires based on the content of the user responses to obtain further information relevant to proper and concise evaluation.

The responses and the personal information obtained from the user is then stored in the user account. Based on the information, the the AI agent software performs an algorithmic analysis to assess the user's needs and to create and deliver a therapy session to the user based on the user's stated or identified needs. For the purpose of monitoring progress and providing the user with feedback, the user's progress is periodically monitored and the user is verbally prompted to complete follow-up evaluations that are in turn compared to the previously entered evaluations in order to track the user's progress as compared to the initial evaluation. Furthermore, progress evaluations must be completed and submitted by the individual in order that follow-up therapy sessions are delivered, which are automatically created and released by the system.

Figure 2:
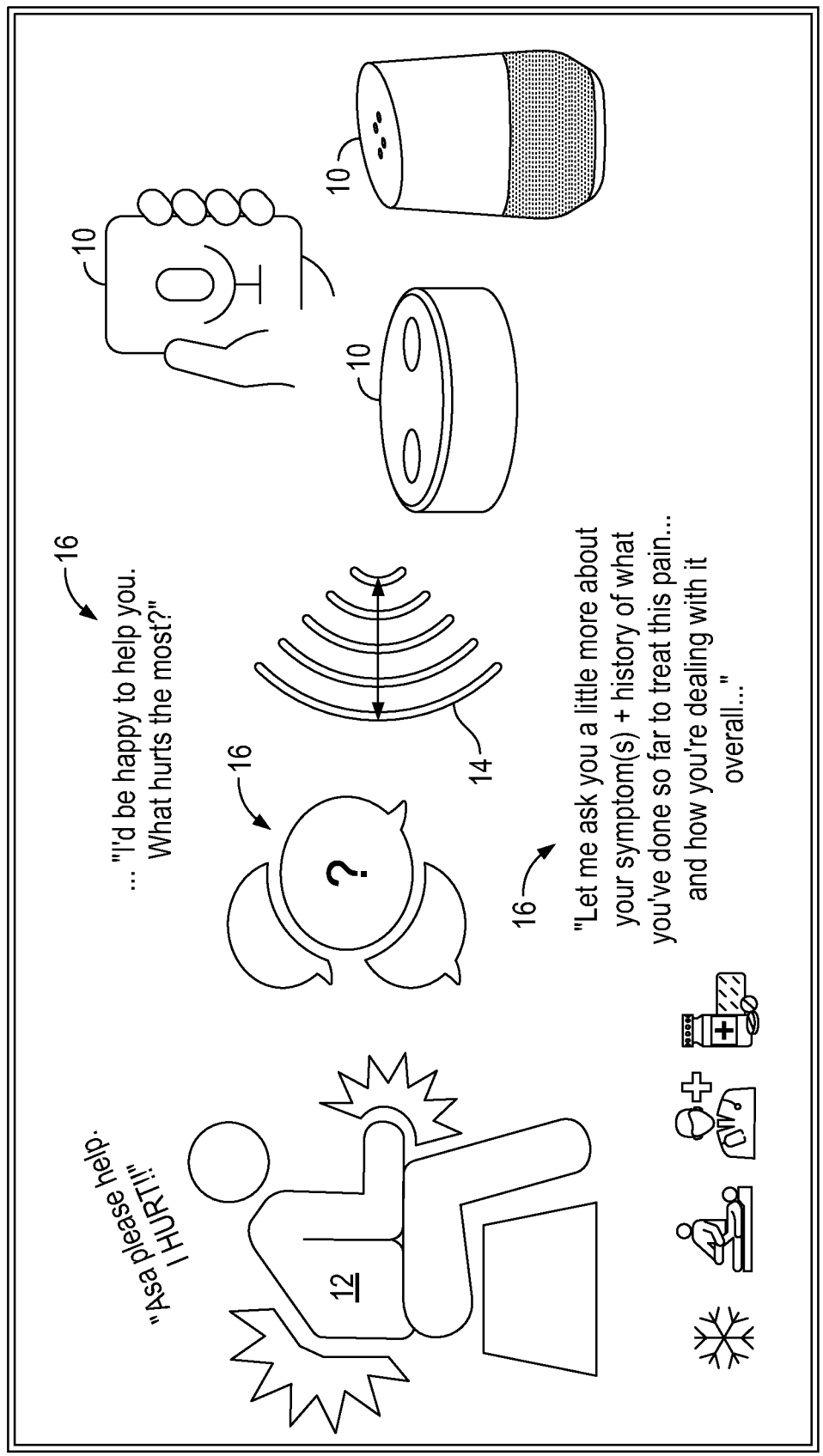
FIG. 2 is a schematic diagram representing the system and an initial input process in the system of the present invention.

Turning now to the figures, FIGS. 1 and 2 depict schematic representations of the system 100 of the present invention. The method and system is implemented via an electronic communications network such as the Internet 106 using various connections via WIFI, Bluetooth, Ethernet and the like, as is well known in the art. As the primary user interface, the exemplary system employs a voice-activated personal assistant device 10 such as Siri™ which operates on Apple™ licensed mobile electronic communication systems, as well as Alexa™, Google™, Cortana™, etc. These VAPA devices may comprise simple VAPA enabled speaker devices 10, VAPA enabled mobile devices (phones 10A, tablets 10B), or VAPA enabled desktop or laptop computer devices 10C. During the initial verbal interaction, background questions regarding biometric data are asked and employed for establishing a user account. It should be appreciated that the method of the present invention may be implemented in a number of different variations, all of which are intended to fall within the scope of the present invention. Preferably, the artificial intelligent agent system for implementing the method of the present invention is hosted on server 104 that is connected to and accessible through an electronic communications network such as the Internet 106 or any other suitable wide area, accessible network. The user(s) then access(es) and interact(s) with the system 100 via a local VAPA enabled device 10 as described above for the purpose of providing interactive voice responses 14 to capture user information, provide their recommended therapy and to follow up with subsequent therapy sessions and evaluations. The general intent only requires that the system 100 be provided and accessible by the user(s) without the need for an intermediary or professional to input and maintain the user data.

Figure 3:
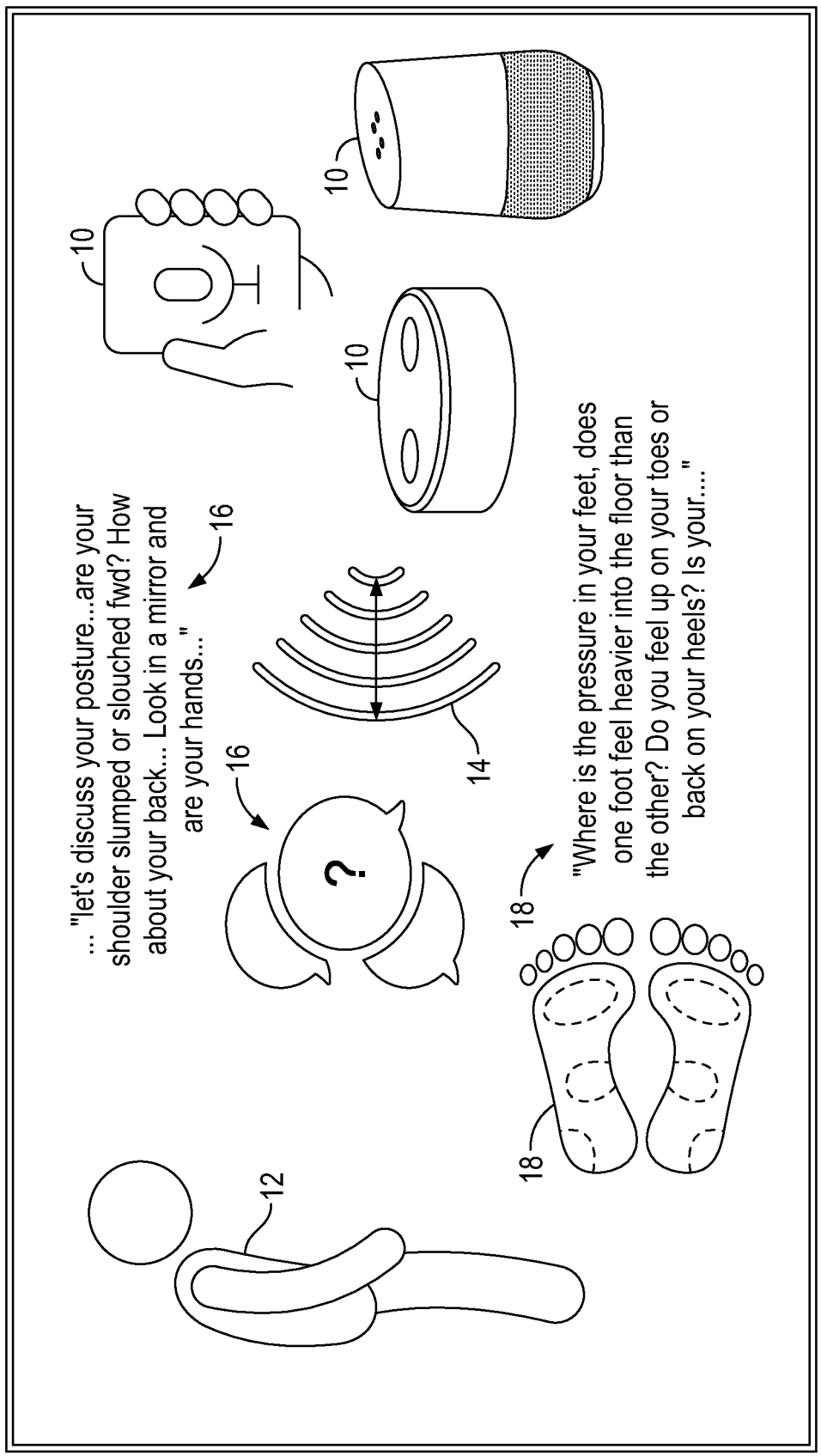
FIG. 3 is a schematic diagram representing a sample of an interactive inquiry and exchange that is completed by the user for determining the user's physiological needs.

Once the user account has been established, the user 12 then states the type of therapy that they wish to obtain. Based on the basic user information that was captured and the user's therapy preferences identified, the system then prompts the user to respond to a number of questions 16 regarding their physical condition, activity level, anatomical posture and pain symptoms. FIG. 2 for example, depicts question prompts 16 directed at obtaining the users current symptoms and the present manner in which the user has attempted to remedy the pain. For purposes of the present disclosure and drawings, the proprietary VAPA system is herein referred to as ASA™, which translates in several languages to "healer" or "physician". The artificial intelligent agent then begins an analysis to interactively identify a proper pathway in which to continue inquiry based on the previous responses. In this case, FIG. 3 depicts questions 16 identifying the physical activities in which the user participates and the user's current posture. Based on those responses, the artificial intelligence agent determines further relevant follow up questions such as the manner in which a user bears weight on their feet 18

Figure 4:
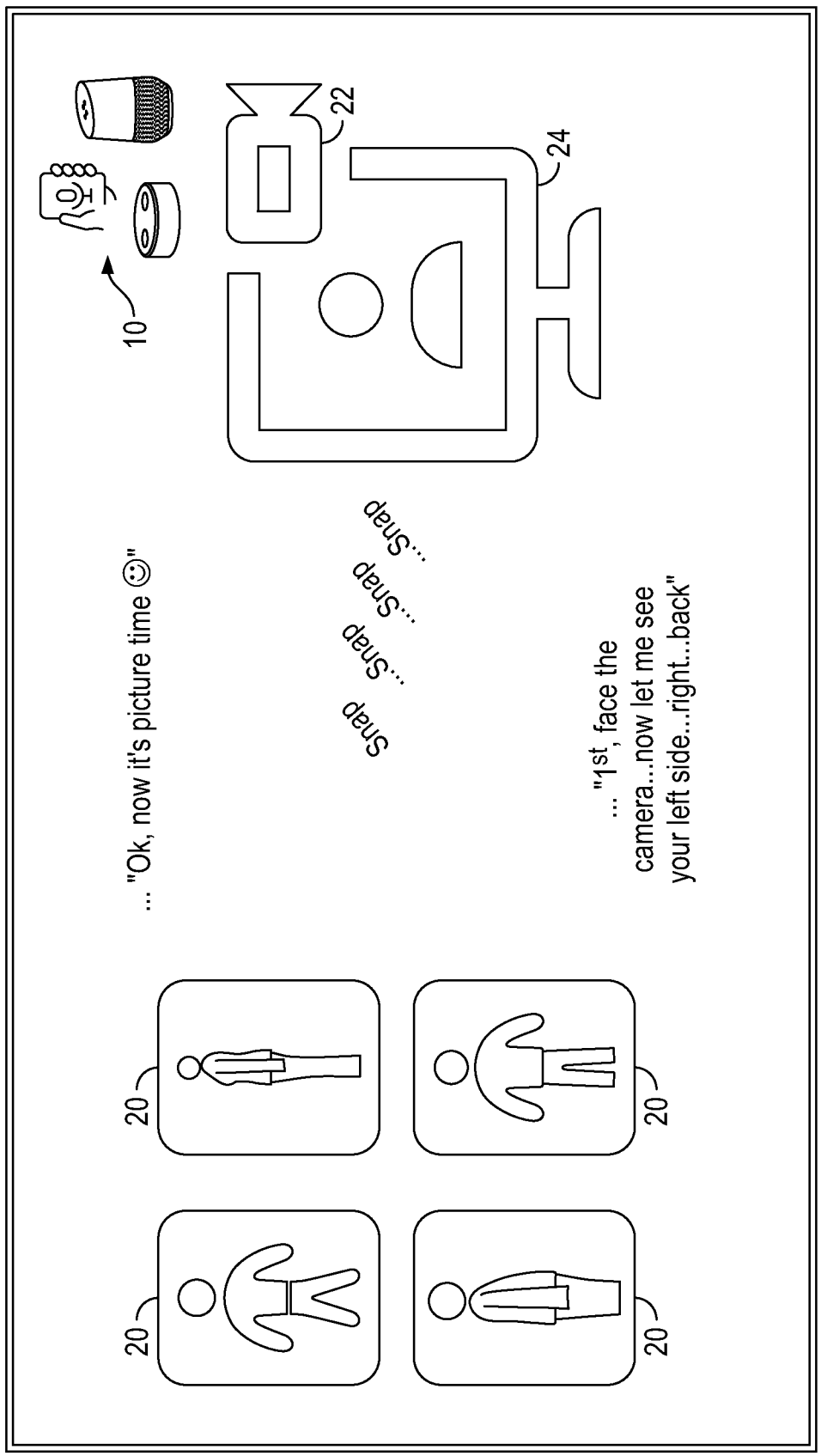
FIG. 4 is a schematic diagram representing a sample input screen for uploading user prepared images in the system of the present invention.
Figure 5:
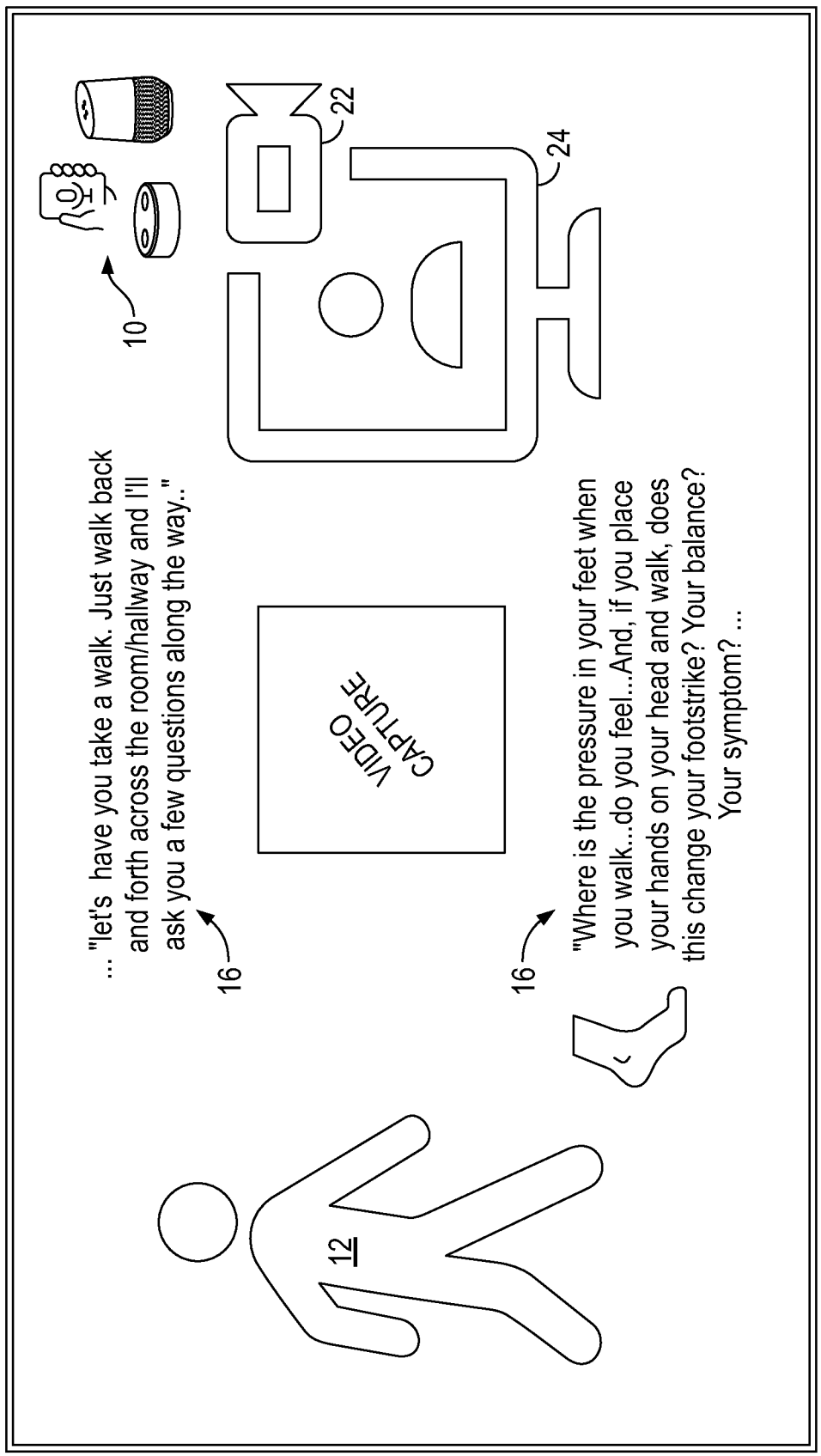
FIG. 5 is a schematic diagram representing a sample input screen for uploading video capture in the system of the present invention.

As depicted at FIG. 4, the system 10 also includes a feature whereby a user may generate postural images 20 of their body using a user provided camera 22 that is in electronic communication with the network either directly or via an additional computer interface or mobile app 24. The images in turn facilitate the direct evaluation of the user's posture as will be described more fully below. Further, as depicted at FIG. 5, the system may then ask the user to provide a video capture of the user walking while asking additional questions 16 related to the manner in which the user walks in addition to further questions regarding their assessment of their current fitness levels and the severity of their symptoms. This information is used in AI-based gait analysis. After the information obtained, it is stored in a user account to create a reference point from which the evaluation process may begin.

Figure 6:
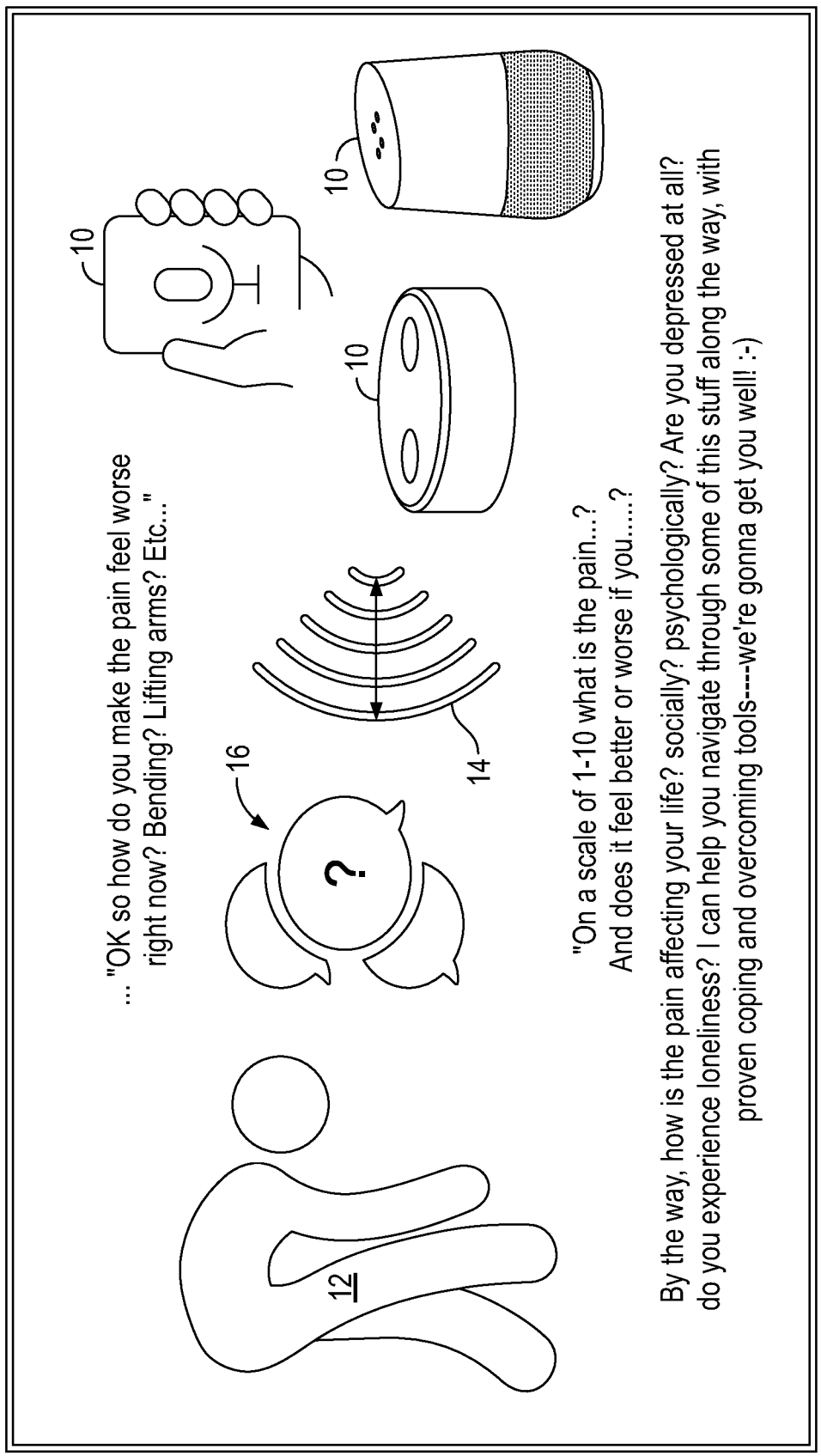
FIG. 6 is a schematic diagram representing the user executing various range of motion exercises and providing feedback for the building of an appropriate therapy routine.

Given the symptoms, the artificial intelligence agent begins to determine appropriate movements and request that the user perform the movements to further refine the evaluation as depicted at FIG. 6. After the user completes the questions and provides the system with all of the information needed to evaluate the user's complaint, condition, and symptoms, the system processes the information and evaluates the user's therapy needs without any further input from the individual. The artificial intelligence agent analyzes the responses provided by the user, the system selects a coordinated series of predefined therapy routines and/or lifestyle recommendations, each consisting of predefined exercises and specs of each exercise (i.e. sets, repetitions, time) specifically for each routine, all designed to systematically correct posture deviations, muscular imbalances and biomechanical compensations and to relieve the user's symptoms, in addition to modifying lifestyle, habits, and behavior of the user. These therapy routines are stored in the remote database, or another database (not shown) and are accessible to the AI system.

Figure 7:
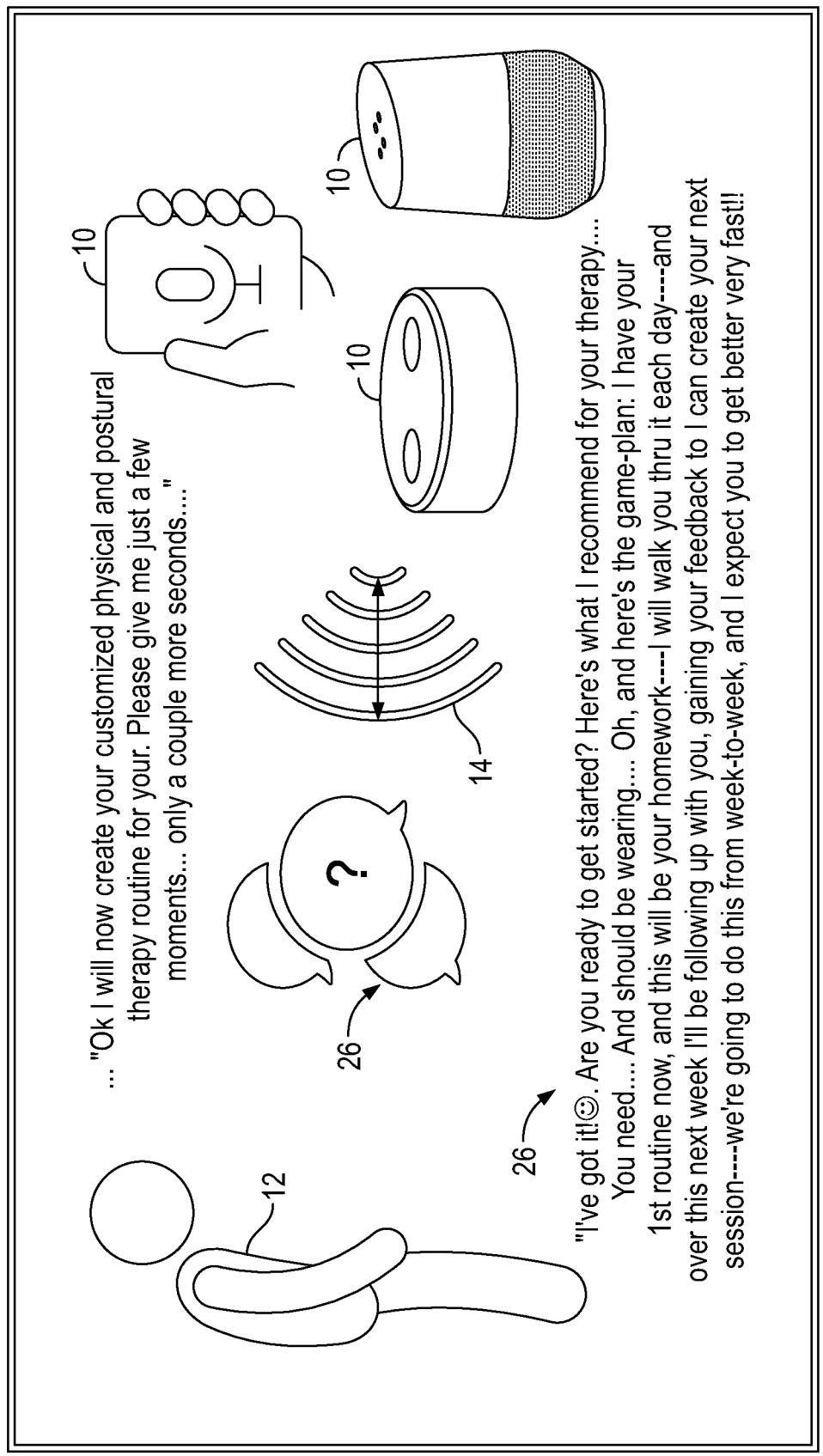
FIG. 7 is a schematic diagram representing a guided therapy session delivered by the system of the present invention.

At FIG. 7, once the processing is completed and the recommended therapy is identified, the system converts the routine into a verbal set of instructions and interactions and delivers the therapy routine 26 to the user via the voice activated personal assistant and (if applicable) video screen. This process only takes seconds and is therefore delivered in real time to the user(s). The system, via the artificial intelligence agent then verbally directs the user through the therapy routines as if the user were interacting with an actual human therapist. As the user progresses through the routine, feedback is obtained from the user and the routine is adjusted based on progression of therapy and the feedback obtained. The user also can log in to a conventional computer system or mobile app at anytime and view the most current session as well as all archived sessions. All multimedia pertaining to the specific personalized routines is stored and the user can view or print out the instructions for their therapy session.

The therapy sessions are delivered to the user in the form of voice instructions delivered over the voice activated personal assistant (VAPA) where the recommended exercises are described in detail allowing time for completion of exercised and establishing voice prompts to move to the next exercise. If needed, the user is directed to online resources to identify the proper form to be used when completing the exercise as well as text providing the user with instructions for completing the exercise. Users may also be provided with access to video clips of a therapist performing the exercise properly, and/or a practitioner giving recommendations. An initial therapy session may include several such exercises that were identified by the system to particularly address the symptoms and muscular conditions of the user. The intent is that based on user responses to the voice inquiries, the system automatically evaluates the user's complaint and provides a tailored custom therapy session that the user implements in a self-directed fashion.

The system is also configured to provide the user with updated therapy sessions as they progress through their therapy and recovery. In this manner, the system automatically follows up with verbal reminders and updates sessions that direct the user to interactively step through the same series of inquiries to determine feedback and to complete an updated evaluation. Once this information is collected, an updated therapy session is created and delivered, and all information is stored in the user account alongside the user's initial evaluation whereby the results of the updated evaluation can be compared to the results of the initial evaluation. The purpose of this is to replicate the process of face-to-face therapy sessions whereas an individual only receives new routines once their input is given and the assessment is made. In this manner, as the user proceeds through the sequential therapy sessions and periodically updates the evaluations they receive immediate feedback in a form of a new therapy session, further instructions, and an update regarding their overall progress towards their goal of living pain free.

The artificial intelligence agent is modeled on human thought processes, via human-to-machine voice interactions and smart-displays, which has the ability to solve problems where other therapeutic systems cannot, by learning and reasoning simultaneously for multiple users. This is accomplished whereby the artificial intelligence agent (ASA), via the voice-recognition, focuses on priorities identified by each user, during 1) evaluation/intake, 2) guidance/coaching through therapy & training sessions, and 3) follow up progress reporting. The system decisions follow dynamic algorithms based on complex patterns which utilize the following foundational rules structured based on Exercise Sequencing for both therapy/pain-relief and postural strength training/prevention via system observation (voice communication and if applicable, but not required, image and video capture) and via powerful feedback loops (giving users real-time info about their body, while the system learns). The system further applies a Deviation Reduction Theorem to reduce plane deviations via frames of reference to regain lost motion and/or restore neuromuscular function. The system also applies a Muscular Hold Theorem: a. COG, b. Proximal to Distal, c. Postural and Dynamic groups, d. Stabilize and Strengthen.

The artificial intelligence agent accordingly applies proven therapeutic exercise and modality sciences for pain-relief, weight-loss, and strength-training while implementing macro-program sequencing using a proprietary substitution system that is based on initial contraindications, and client feedback via voice communication). The autonomous divergent learning guides the user interactions to leverage knowledge of postural therapists, physical therapists, fitness trainers, and MD's in real time via the artificial intelligence agent which is based on Artificial Neural Networks/Deep Artificial Learning (or "Deep Learning") that crunches sets of data of enormous size and includes vision tasks, image classification, object detection, body/posture recognition, and gait recognition. In addition, it analyzes a plethora of evaluation and medical conditions via libraries of connected data and sifts through such large databases and applies appropriate therapy/fitness sequencing, recommendations, and protocols, via any voice assistant system. This system is implemented in a uniform open platform that scales across all voice control systems, capitalizing on smart-displays and improved functionality leveraging more robust speakers and far-field microphones.

The system of the present disclosure follows a biopsychosocial model, and is therefore also capable of utilizing its intelligence for mental health and emotional support as well as helping identify and change social behaviors. Many physical pains, as well as metabolic syndrome (high blood pressure, blood sugar, cholesterol, excess body fat), are often accompanied by negative social and psychological factors. ASA therefore is not merely limited to the biomedical model, but also helps individuals in modifying risky behaviors and adopting healthy lifestyle choice. This includes an entire motivational support system to help the user in adopting the said recommendations by the AI agent.

The method and system of the present invention also includes another feature not previously available in prior art evaluation systems. Specifically, the method and system of the present invention employs a technology that improves the process of in-clinic and video therapy programs typically offered only at a therapy facility. The present system provides a unique method of evaluating the user's posture by allowing a user to upload predefined pictures or have posture pictures taken with camera (if present on voice assistant platform). In this manner, the present invention provides the user with a guide that the user follows to create a set of images that are compatible with the system. The user then employs the interface to upload their pictures into the system. The AI system automatically evaluates posture and gives feedback to the user, in addition to allowing user to manipulate the posture alignment guide tool to visually identify misalignment of the body and for comparison of posture before and after treatment.

The system also stores the user pictures into the user account as they are uploaded and preserves them for comparison and tracking of progress. In this manner images from before and after therapy sessions can be compared in a side-by-side manner to provide the user with visual feedback regarding their progress through the therapy sessions. Finally, the uploaded images may be displayed in connection with preprepared images stored within said interface and depicting correct posture, wherein said user can observe their body posture as compared to correct body posture.

In a similar manner, users can upload video clips for gait analysis, in accordance with the directions given to walk to and from the camera with differing arm positions, backwards, and sideways, and the uploaded video triggers a practitioner to evaluate the video and then upload the appropriate therapeutic regimen. In addition, the AI can complete an automatic analysis of the user's gait, without any help from a practitioner, and the AI agent then describes the gait disparities and dysfunctions, after its complete automated and in-real-time gait analysis.

It can therefore be seen that the present invention provides a novel method and system for delivering customized therapy sessions simultaneously to multiple users to address specific user symptoms in a cost effective and efficient manner that also dramatically reduces the need for costly therapist involvement. Further, the present invention provides an automated online system whereby a user can upload images and interactively evaluated their posture thereby allowing them to identify various posture defects and misalignments as was previously available only through an office visit with a professional therapist. For these reasons, the instant invention is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A method for delivering a customized physical and/or mental health therapy routine and/or recommendations to a user:
    establishing a user account;
    establishing verbal user interaction with a server via a voice activated personal assistant device in communication with said server;
    employing an artificial intelligence agent running on said server to interactively engage and guide said user to verbally complete a user profile by generating voice inquiries and recording user verbal responses to verbally obtain personal information including at least the user's physical attributes, personal data, physical condition, and physical and/or mental health symptoms,
    said artificial intelligence agent interactively guiding, evaluating and modifying said engagements based on said user verbal responses to interactively assess the user individual needs and symptoms;
    storing said user profile including said personal information in said user account in a database in communication with said server;
    employing said artificial intelligence agent to evaluate said user profile and said personal information, and to develop a customized therapy routine for said user;
    employing said artificial intelligence agent to generate one or more verbal interactive therapy prompts based on said customized therapy routine;
    delivering said verbal interactive therapy prompts to said user through said voice activated personal assistant device;
    periodically monitoring the user's progress by employing said artificial intelligence agent to interactively verbally prompting said user to verbally respond to verbal feedback inquiries and recording said user verbal feedback responses;
    storing said user verbal feedback responses; and
    employing said artificial intelligence agent to evaluate said user verbal feedback responses, to adapt said customized therapy routine, to generate new verbal interactive therapy prompts and interactively deliver said new verbal interactive therapy prompts to said user through said voice activated personal assistant device.

2. The method of claim 1, wherein said artificial intelligence agent requests verbal feedback from said user as said user is guided through each routine, said feedback employed by an artificial intelligence agent to create a modified routine based on said verbal feedback.

3. The method of claim 2, further comprising the steps of:
    providing an electronic camera in communication with said server,
    employing said artificial intelligence agent to verbally prompt said user to generate a said set of postural images of said user's body using said camera, and
    employing said artificial intelligence agent to evaluate said images to further assist in generating said customized therapy routine.

4. The method of claim 3, wherein said step of periodically monitoring user progress includes generating and delivering verbal prompts to generate an updated set of postural images, said artificial intelligence agent evaluating said updated images to further assist in generating said customized therapy routine.

5. The method of claim 2, further comprising the step of obtaining personal information further comprises the steps of:
    providing an electronic video camera in communication with said server,
    employing said artificial intelligence agent to verbally prompt said user to generate a set of gait videos of said user in motion,
    employing said artificial intelligence agent to evaluate said gait videos to further assist in generating said customized therapy routine.

6. The method of claim 5, wherein said step of periodically monitoring said user progress includes employing said artificial intelligence agent to verbally prompt said user to generate an updated set of gait videos, said artificial intelligence agent evaluating said updated videos to further assist in generating said customized therapy routine.

7. The method of claim 1, further comprising the steps of:
    providing an electronic camera in communication with said server,
    employing said artificial intelligence agent to verbally prompt said user to generate a said set of postural images of said user's body using said camera, and
    employing said artificial intelligence agent to evaluate said images to further assist in generating said customized therapy routine.

8. The method of claim 7, wherein said step of periodically monitoring user progress includes generating and delivering verbal prompts to generate an updated set of postural images, said artificial intelligence agent evaluating said updated images to further assist in generating said customized therapy routine.

9. The method of claim 7, further comprising the step of obtaining personal information further comprises the steps of:
   providing an electronic video camera in communication with said server,
   employing said artificial intelligence agent to verbally prompt said user to generate a set of gait videos of said user in motion,
   employing said artificial intelligence agent to evaluate said gait videos to further assist in generating said customized therapy routine.

10. The method of claim 9, wherein said step of periodically monitoring said user progress includes employing said artificial intelligence agent to verbally prompt said user to generate an updated set of gait videos, said artificial intelligence agent evaluating said updated videos to further assist in generating said customized therapy routine.

11. The method of claim 1, further comprising the steps of:
   providing an electronic video camera in communication with said server,
   employing said artificial intelligence agent to verbally prompt said user to generate a set of gait videos of said user in motion,
   employing said artificial intelligence agent to evaluate said gait videos to further assist in generating said customized therapy routine.

12. The method of claim 11, wherein said step of periodically monitoring said user progress includes employing said artificial intelligence agent to verbally prompt said user to generate an updated set of gait videos, said artificial intelligence agent evaluating said updated videos to further assist in generating said customized therapy routine.

* * * * *